United States Patent [19]

Wilkins et al.

[11] Patent Number: 4,863,852

[45] Date of Patent: Sep. 5, 1989

[54] METHOD OF DETECTING, ISOLATING AND PURIFYING CLOSTRIDIUM DIFFICILE TOXIN A AND ITS RECEPTORS

[75] Inventors: Tracy D. Wilkins; Howard C. Krivan, both of Blacksburg, Va.

[73] Assignee: Virginia Tech Intellectual Properties, Inc., Blacksburg, Va.

[21] Appl. No.: 828,404

[22] Filed: Feb. 11, 1986

Related U.S. Application Data

[63] Continuation-in-part of Ser. No. 752,330, Jul. 3, 1985, abandoned.

[51] Int. Cl.[4] .................... G01N 33/569; C12Q 1/04; C12Q 1/06

[52] U.S. Cl. .......................................... 435/7; 435/34; 435/39; 435/803; 435/842; 530/413; 530/825; 436/520; 436/534; 436/829

[58] Field of Search .................... 435/34, 7, 262, 280, 435/803, 810, 842, 820, 39; 436/520, 829, 533, 534; 530/412, 413, 825

[56] References Cited

U.S. PATENT DOCUMENTS 4,533,630 8/1985 Wilkins et al. .......................... 435/7

FOREIGN PATENT DOCUMENTS 153519 4/1985 European Pat. Off. .

OTHER PUBLICATIONS

An Introduction to Separation Science, 1973, John Wiley and Sons, New York, pp. 402-410.

Chemical Abstract 100:187010b (1984), abstracting Stephen et al., Biochen. Soc. Trans. 12(2), 194–5 (1984).

Chemical Abstract 99:86229k (1983), abstracting Viscidi et al., J. Clin. Microbiol. 18(2), 242–7 (1983).

Spiro, R. et al., "Occurrence of α–D–Galactosyl Residues in the Thyroglobulins from Several Species", J. Biol. Chem., 259:9858–9866 (1984).

Wilkins et al., "Clostridial Toxins Active Locally in the Gastrointestinal Tract", *Microbial Toxins and Diarrhoeal Disease, Pitman, London (Ciba Foundation Symposium 112), pp. 230–241 (Mar. 1985).*

Lonroth et al., "Toxin A of *Clostridium Difficile:* Production, Purification and Effect in Mouse Intestine", Acta Path. Microbiol. Immunol. Scand. Sect B, 91: 395–400 (1983).

Lyerly, et al., "Enzyme–Linked Immunosorbent Assay for *Difficile* Toxin A", J. Clin. Microbial., 17: 72–78 (1983).

Thelestram, M. et al., "Cytopathogenic Action of *Clostridium Difficile* Toxins", J. Toxicol.–Toxin Reviews, 3: 139–180 (1984).

*Primary Examiner*—Esther M. Kepplinger

*Attorney, Agent, or Firm*—Seidel, Gonda, Lavorgna & Monaco

[57] ABSTRACT

A method is provided for detecting the presence of *C. difficile* toxin A. Stool or other appropriate specimen is contacted with a reagent containing an available non-reducing galactose-alpha-1-3-galactosyl structure, which is a specific receptor for toxin A. The reagent may be intact cells, cell membranes, membrane fractions containing the toxin A receptor structure, glycoconjugates, as well as the purified toxin A receptor per se. Binding of toxin A is determined by conventional assay techniques. The method may also be used to isolate and purify toxin A. Conversely, immobilized toxin A is used to detect, isolate, or purify biological materials of interest containing the receptor structure.

29 Claims, 1 Drawing Sheet

A    B

A    B

METHOD OF DETECTING, ISOLATING AND PURIFYING CLOSTRIDIUM DIFFICILE TOXIN A AND ITS RECEPTORS

REFERENCE TO GOVERNMENT GRANT

The invention was supported in part by grant AI 15749 from the National Institutes of Health This is a continuation-in-part of application Ser. No. 752,330, filed July 3, 1985, now abandoned.

FIELD OF THE INVENTION

This invention relate generally to the detection, isolation, and purification of *Clostridium difficile* toxin A. The invention also relates to the detection, isolation and purification of materials containing a non-reducing galactose-alpha-1-3galactosyl structure which acts as a receptor for toxin A.

BACKGROUND OF THE INVENTION

*Clostridium difficile* causes disease within the gastrointestinal tract, usually following an alteration of the intestinal microecology. The pathogenic role of toxigenic *C. difficile* in antibiotic-associated pseudomembranous colitis in humans is well established. Disease symptoms vary with the source of the pathogen, antibiotic exposure, toxin production, and patient age.

*C. difficile* produces two toxins, designated A and B. The toxins are implicated in the etiology of the disease. They can be separated by ion exchange chromatography and identified according to their elution behavior from DEAE ion exchange. Toxin A elutes at 0.15M NaCl, and may be further purified by isoelectric precipitation. Toxin B elutes at 0.3M NaCl, and is further purified by affinity chromatography. Toxin A is primarily an enterotoxin with slight cytotoxic activity, whereas toxin B is a potent cytotoxin. Toxin A causes extensive damage to the gut mucosa, as well as accumulation of fluid in the intestinal tract It is believed that the primary event in the mechanism of *C. difficile* infection involves the specific binding to receptors on the intestinal cell surface. However, "receptor" as used herein means simply the chemical structure which binds toxin A without regard to whether or not that structure is in fact implicated in the disease-causing process.

*C. difficile*-associated intestinal disease has been reported in infants, and in adults in the absence of antibiotic therapy. Moreover, *C. difficile* is one of the most common bacterial enteropathogens found in stool specimens in hospitals. The organism has been reported to be one of the most commonly detected bacterial pathogens of enteric disease. In the United States, the disease now exceeds the total number of illnesses caused by *C. botulinum, C. tetani* and *C. perfringens.*

*C. difficile* causes pseudomembranous colitis in humans as a result of the elimination of the normal flora of the colon by antibiotic usage and growth of this toxin-producing bacterium. The disease usually occurs in hospitalized patients where it causes a massive diahhrea with extensive inflammation of the colon. Without proper treatment, the patient is likely to die. Treatment is based on a proper diagnosis which is accomplished by establishing the presence of the toxin and demonstrating the characteristic lesions in the colon.

Recent success in the purification of toxins A and B has stimulated a great deal of interest in their biological properties. Further study may lead to an understanding of how the toxins cause disease. However, existing methods for purifying these proteins are costly, require skilled personnel, and demand several days to obtain pure toxin.

The existing methods for detecting pathogenic *C. difficile* are inadequate. One such test involves the culture of human feces, which requires specialized facilities for a long period of incubation. This test suffers from interference by non-pathogenic *C. difficile* strains, namely strains not producing toxin. The test is costly, time-consuming, and can only be performed in larger, well-equipped hospitals or in private laboratories.

A more innovation in the detection of pathogenic *C. difficile* involves the use of specific antisera to toxin A coated onto latex beads. Lyerly, et al, *A.J. Clin. Microbiol.* 17:72–78 (1983). The resulting immobilized antibody agglutinates soluble toxin A. The agglutination of the large latex beads can be easily seen, indicating the presence of toxin A in the sample However, the method is expensive since it relies upon costly monospecific antibodies to toxin A.

What is needed is a simple, rapid and inexpensive method for obtaining highly purified toxin A, and a simple, rapid and inexpensive test for detecting the presence of toxin A which can be performed in any hospital laboratory.

SUMMARY OF THE INVENTION

We have found that *C. difficile* enterotoxin (toxin A) is easily and reproducibly detected and/or purified by contacting a sample suspected of containing the toxin with a reagent containing an available non-reducing galactose-alpha-1-3-galactosyl structure (hereinafter "Gal-alpha-1-3Gal structure"). The toxin A receptor appears to be a glycoconjugate containing the non-reducing sequence galactose-alpha 1-3-galactose-beta-1-4-N-acetyl glucosamine (typically abbreviated as Gal-alpha-1-3Gal-beta-1-4GlcNAc). It is believed that at least the Gal-alpha-1-3Gal structure is necessary for binding toxin A and that the sequence is terminal on the glycoconjugate. Quantitative binding of toxin A with the receptor occurs rapidly, specifically, reliably, and reversibly in a dose-dependent manner. The receptor can therefore be used for large-scale purification of toxin A, as well as for the detection and isolation of minute toxin quantities.

A method for detecting *C. difficile* toxin A comprises (a) contacting a specimen with a reagent containing an available non-reducing galactose-alpha-1-3-galactosyl structure, and (b) assaying for binding of *C. difficile* toxin A to the reagent.

Conversely, toxin A is used according to the invention to detect, isolate, and/or purify materials in which the unique receptor structure is available, or can be made available. Such materials include rare biological molecules, carbohydrates, proteins, glycoproteins, glycolipids, conjugates, and the like. They can be detected and/or purified even when present in very small quantities because of the specificity, reliability and reversibility of toxin A-receptor binding.

A method for isolating or purifying a reagent containing an available non-reducing galactose-alpha-1-3-galactosyl structure comprises (a) contacting materials which may contain the reagent with immobilized *C. difficile* toxin A at a temperature favoring reversible binding of the reagent to toxin A; (b) increasing the temperature to release the reagent from the immobilized toxin A; and (c) eluting the reagent Conversely, a method for isolating or purifying toxin A comprises contacting a source of toxin A with an immobilized reagent containing an available non-reducing galactose-alpha-1-3-galactosyl structure at a temperature favoring reversible binding of toxin A to the immobilized reagent; (b) increasing the temperature to release the toxin A bound to the immobilized reagent; and (c) eluting toxin A.

Binding is temperature dependent. It is therefore preferably carried out in the cold, or using cold reagents Generally, the binding reaction occurs favorably below room temperature (about 20° C). Temperatures of 0–15° are preferred, 4° C. being most preferred. The sensitivity of the receptor to toxin A has been found to be 8–10 times greater at low temperatures than at room temperature. When receptor-bound toxin A is warmed above room temperature (20° C.) the toxin begins to disassociate from the receptor in an undenatured form. Warming to about 30° C. or higher will release the toxin, with 30–37° C. being preferred. The result is a rapid one step purification technique for toxin A, as well as for reagents containing the galactose- alpha-1-3-galactosyl structure. The process provides very high yields of very pure product

DETAILED DESCRIPTION OF THE INVENTION

Figure 1:
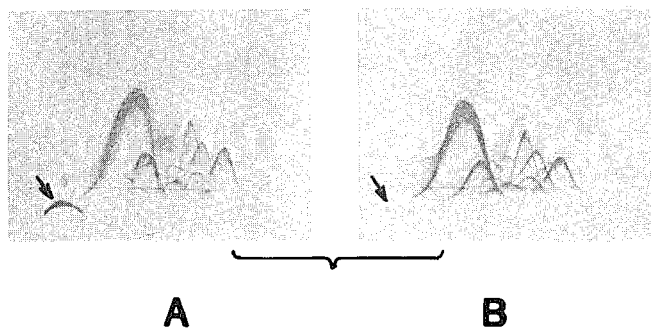
FIG. 1 is an analysis of C. difficile strain 10463 culture filtrate adsorbed with hamster brush border membranes and rabbit erythrocytes. The upper portion of the gel in each plate contained 0.1 ml of goat antiserum against *C. difficile* strain 10463. In panel A, the well contained 50 micrograms of strain 10463 culture filtrate. The arrow shows the location of the toxin immunoprecipitin arc. In panel B, the well contained 50 micrograms of strain 10463 culture filtrate adsorbed with 25 micrograms of packed hamster brush border membranes. Identical results were obtained with 25 micrograms of packed rabbit erythrocyte membranes. The absence of the toxin A arc (arrow) in panel B demonstrates that the toxin was removed by each cell type.
Figure 2:
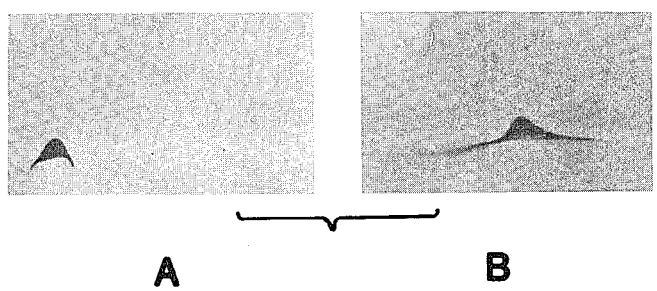
FIG. 2 is an analysis of *C. difficile* strain 10463 purified toxin A combined with Triton X-100 solubilized extract from rabbit erythrocyte membranes. The upper portion of the gel in each plate contained 0.1 ml of goat antiserum against *C. difficile* strain 10463 culture filtrate. In panel A, the well contained 15 micrograms of toxin A combined with 1% Triton X-100 In panel B, the well contained 15 micrograms of toxin A combined with 1% Triton X-100-solubilized extract. The altered migration of the toxin immunoprecipitin arc is observed in panel B.

By "ghost" is meant the delicate discoid membrane obtained after removal of hemoglobin from an erythrocyte.

By "reagent" with regard to the non-reducing galactose-alpha-1-3-galactosyl structure is meant any molecule, cell membrane, tissue, bead, liposome, solid support (synthetic or natural) or any other material containing, including, or having affixed thereto the aforesaid chemical structure in an available form for binding with toxin A.

By "specimen" is meant any preparation containing tissue, cells, blood, stool or other material that may contain *C. difficile* toxin A.

Any suitable material containing the non-reducing galactose-alpha-1-3-galactosyl sequence may be employed as the reagent according to the present invention to detect, isolate or purify toxin A. It is believed that toxin A has multiple binding sites similar to lectins and that there is a structural requirement for a galactose-alpha-1-3-galactosyl moiety for the toxin to bind receptor.

Moreover, we have found that all such materials tested which bind toxin A contain the further sugar moiety N-acetyl glucosamine connected by a beta 1–4 linkage such that the full receptor structure sequence is believed to be the terminal sequence Gal-alpha-1-3Gal-1-4GlcNAc.

It has been found that the brush border membranes of animals, and erythrocytes and erythrocyte ghost membranes of rabbits, contain the Gal-alpha-1-3Gal structure. These materials quantitativly bind toxin A. Examination of the cell surface of rabbit erythrocytes with lectins, immunological probes, and specific glycosidases demonstrates the presence of a high concentration of terminal alpha-linked galactose which specifically binds toxin A. Rabbit ghosts offer an advantage over erythrocytes in that hemoglobin leakage during purification is avoided. Calf erythrocytes also contain receptors binding toxin A, but the receptors are active only after extraction from erythrocyte membranes by, for example, non-ionic detergents. Hamster brush border membranes contain high concentrations of the receptor structure. Rabbit erythrocytes have the highest concentration of the receptor structure of the materials tested.

Enzyme-linked immunosorbent assay (ELISA) indicates that 95% of the toxin A binding activity of receptor-containing membranes is removed by detergent treatment. The loss of binding activity from the membrane material is accompanied by the appearance of toxin-binding activity in the membrane extract. Soluble receptor activity is completely destroyed by alpha galactosidase treatment.

Thyroglobulin glycoproteins have been found to contain a complex carbohydrate unit that yields oligosaccharides containing the Gal-alpha-1-3Gal structure following partial acid hydrolysis. Calf, sheep, pig, and dog thyroglobulins have been found to contain significant concentrations of the receptor while rat, rabbit, and guinea pig thyroglobulin contains lesser quantities. Another glycoprotein called laminin, which occurs in almost all cells, has also been found to bind toxin A. Lipids which contain the structure Gal-alpha-1-3Gal, or from which the structure can be made available, also can act as a receptor of this invention. Collagen, a glycoprotein which occurs in animal tissue, has also been demonstrated to bind toxin A.

Other materials which do not exhibit the receptor activity of this invention can also be used as a reagent if they contain a unit from which the Gal-alpha-1-3Gal structure can be formed, freed or extracted to be available to bind toxin A. For example, human type B erythrocytes, which contain the B antigen Gal-alpha-1-3-(Fuc-alpha-1-2)Gal, did not bind toxin A. Removal of the fucose moiety with fucosidase results in the receptor structure and the appearance of toxin A binding activity. Likewise, calf erythrocytes, which initially exhibited no toxin A binding activity, rapidly bound toxin A after detergent treatment (Triton X-100, Sigma Chemical Co.). This indicates that the Gal-alpha-1-3Gal structure exists on bovine erythrocytes, but can only be detected after detergent solubolization.

The method of this invention for detecting, isolating, or purifying toxin A, or conversely, for using toxin A to detect, isolate or purify materials having the available receptor structure, is a gentle, efficient, single-step procedure that yields highly purified product. The process can be scaled up to isolate or purify gram quantities of product within a few hours.

Because the glycoconjugate is so specific, toxic A purified by the method of the present invention is homogeneous, as judged by immunoelectrophoresis and gradient polyacrylamide gel electrophoresis. The product is identical to toxin A purified by conventional methods, as determined by immunodiffusion analysis. The affinity-purified toxin A of the invention is cytotoxic in tissue culture and enterotoxic and lethal when given orally to hamsters. Toxin-binding capacity is directly proportional to the amount of the receptor material used in the procedure.

Generally, any suitable method for contacting the Gal-alpha-1-3Gal structure-containing reagent and an appropriate specimen may be employed to detect, isolate or purify toxin A. Conversely, any suitable method for contacting toxin A and the reagent may be employed to detect, isolate or purify the latter. The binding reaction is almost instantaneous. Incubation times from 1-5 minutes are possible, although it is preferred to incubate for 5 minutes to insure complete binding.

To test specimens for the presence of toxin A, the reagent containing the available non-reducing galactose-alpha-1-3galactosyl structure is contacted with the specimen. The extent of toxin A binding is determined by suitable assay. Binding may be assayed by a wide variety of well-known techniques including ELISA, hemagglutination, slide agglutination, slide coagglutination, latex agglutination, surface immobilization and entrapment of the toxin A receptor on particles (e.g., liposomes), indirect immunofluorescence, radioimmune assay, and other techniques known to those skilled in the art. In one embodiment, rabbit erythrocytes or erythrocyte ghosts are contacted with specimen. Thereafter, antisera containing toxin A antibody from another species, e.g. goat, is added to the mixture. Agglutination of cells indicates the presence of toxin A in the specimen. Agglutination of erythrocytes may be seen easily when the reaction is run on a glass slide, in the well of a microtiter plate, or in a test tube. Ghosts are white, and therefore more difficult to see than intact erythrocytes. Thus, they are stained with dyes so that agglutination is more easily seen. Ghosts have the advantage of greater stability.

Membrane-bound toxin A may be further detected by immunofluorescent microscopy. Toxin A antibody linked to a fluorescent dye such as fluoroescein isothiocyanate conjugate may be used. The appearance of fluorescent cells upon examination under a fluorescent microscope indicates the presence of toxin A in the specimen.

Toxin A antibody used in the herein methods may be prepared from crude *C. difficile* toxin. The crude toxin includes both toxins A and B, as well as many other *C. difficile* antigens. Procedures for preparing toxin A antibody against crude *C. difficile* filtrate are known to those skilled in the art. Briefly, a suitable animal, e.g., goat, is immunized with the crude preparation and the resultant elicited antisera is comprised of an antibody mixture which includes antibodies to toxin A.

One such method is described as follows:

Crude toxin A culture filtrate is concentrated 30 times with an XM-100 filter (Amicon, Lexington, MA) and applied to a 5 ×30 cm AcA34 column (LKB, Sweden). The toxin is contained in the void volume, which is further purified by precipitation with 45% saturation of ammonia sulfate at 0° C. to 4° C. Toxoid is prepared by incubating this toxin (1 mg protein/ml, Bio-Rad protein determination, Bio/Rad Laboratories, Richmond, CA) in a final concentration of 0.4%C formaldehyde for 36 hours at 37° C. New Zealand white male rabbits are given two 0.5 ml injections of 1:1 toxoid in Freund's complete adjuvant in the muscles of each rear leg at weekly intervals. Goats may be used in place of rabbits. For female goats one year old, 6 ml injections are given. After three injections, the toxoid is mixed with Freund's incomplete adjuvant and injected weekly for seven more weeks. Antitoxin is detected after 6-10 weeks of injections and reaches maximum titers within eleven weeks. At that time, the toxoid-incomplete Freund's suspension is injected every other week, followed at weekly intervals by 40 ml bleedings. The serum contains the antitoxin to toxin A. The titer of the antibody produced by goats is higher than that of rabbits.

The nontoxin antibodies, (except the antibody to certain non-toxin heat-stable antigens of *C. difficile*) are removed from the antibody mixture by contact with a non-toxic strain of *C. difficile*. The subsequent crude antibody mixture containing toxin A antibody may be used in certain of the assay methods described herein.

Since the above method utilizes crude non-specific antibody to *C. difficile*, it is less costly than detection methods which rely on precipitation of latex beads coated with mono-specific antibody to toxin A. Erythrocytes or ghosts may be added to a large volume of specimen, concentrated by centrifugation, and assayed for adsorption of toxin A. Thus, the present invention is potentially more sensitive than methods employing mono-specific antibody.

Any chemical species containing an available non-reducing Gal-alpha-1-3Gal structure, e.g., thyroglobulin, may be linked to beads and used in place of erythrocytes or ghosts.

Fecal material specimens are prepared as follows. Fecal specimens are diluted in an equal volume of phosphate buffered saline ("PBS"), ph 7.4 and kept frozen at −20° C. until used. The specimens are centrifuged for 15 min. at 15,000 ×g, and the supernatant is tested for the presence of toxin A according to the method of the present invention.

In one embodiment of the invention, a thyroglobulin affinity column is prepared for concentrating toxin A from specimens prior to assay, thereby increasing the sensitivity of the assay. Thyroglobulin contains an available Gal-alpha-1-3Gal structure and readily binds toxin A. Thryoglobulin thus advantageously is linked to latex beads, agarose gel, or other suitable solid phase arranged in the form of a chromatography column. Fecal extract as prepared above is passed through the column at 4° C. Raising the temperature to 37° C. causes any toxin A to elute from the column in substantial pure, highly concentrated form.

The test for the presence of toxin A may also be performed on specimens comprising the purported *C. difficile* organism per se, namely cultured cells isolated from patient feces. Thus, the test specimen may advantageously take the form of a scraping of a colony of suspected bacterium growing on agar medium or other solid surface, or may take the form of an aliquot of a culture of the bacterium growing on a liquid medium.

Toxin A used in the selection of materials useful as reagents in detecting toxin A was prepared according to Example 1, which does not form part of the present invention.

EXAMPLE 1

Preparation of Toxin A

A highly toxigenic strain of *C. difficile*, V.P.I. strain 10463, was obtained from the collection of the Department of Anaerobic Microbiology at Virginia Polytechnic Institute and State University, Blacksburg, Va. This strain was used because it produced more toxin than other *C. difficile* strains which we examined. The organism was grown at 37° C. for 48 hours inside a dialysis sack containing 150 ml of saline suspended in two liters of fresh brain-heart infusion broth according to the method described by Ehrich et al. in 'Production of *Clostridium difficile* Antitoxin', *Infec.Immun.* 28: 1041-1043. The inoculumn consisted of 1.5 ml of a 1:10 dilution of an overnight culture in brain-heart infusion broth. Cells were removed by centrifugation at 8000 × g for 10 min. followed by filtration (0.45 micrometer membrane filter, Millipore Corp, Bedford, Mass.). A culture filtrate and purified homogenous toxin A were prepared according to the method described by Sullivan, et al. in "Purification and Characterization of *Clostridium difficile* Toxin", Infec. Immun. 35: 1032-1040. The filtered culture supernatant (c.a.750 ml) from the previous step was concentrated to 50 ml by ultrafiltration at 40° C., using an XM-100 membrane filter (Amicon Corp., Lexington, MA) with a thin-channel type concentrator. The retentate was washed with 1500 ml of 50 mM Tris-hydrochloride buffer (pH 7.5) at 4° C and concentrated to a final volume of 40–50 ml. The concentrated supernatant was loaded onto a DEAE-Sepharose CL-6B column (2.5 by 10 cm) which had been equilibrated with 50 mM Tris-hydrochloride (pH 7.5). Afer the sample was loaded, the column was washed with 200 ml of 50 mM Tris-hydrochloride (pH 7.5) containing 0.05 M NaCl. The sample was eluted first with a 300-ml linear NaCl gradient in 50 mM Tris-hydrochloride buffer (0.05 to 0.25M NaCl) followed by 150 ml of 50 mM Tris-hydrochloride (pH 7.5) containing 0.3M NaCl. A second 300-ml linear gradient (0.3 to 0.6 m NaCl) in the same buffer followed the 0.3M NaCl wash. The flow rate of the columns was 55 to 60 ml/h (gravity) at 4° C. Fractions (4.2 ml) were collected and assayed for cytotoxicity by using CHO-K1 cells. The fractions containing the highest cytotoxic titers were pooled, filter sterilized, and stored at 4° C. The toxins that eluted in the first and second NaCl gradients were designated toxins A and B, respectively. From 5 to 10 ml of the toxic fractions from the first DEAE gradient (toxin A) was dialyzed against 1 liter of 0.01M sodium acetate buffer (pH 5.5) at 4° C. for 18 to 24 h. The dialysate was centrifuged to recover the precipitate at 169 × g for 10 min, washed with 5 ml of the same acetate buffer, and recentrifuged. The precipitate was solubilized in 5 to 10 ml of 50 mM Tris- hydrochloride, (pH 7.5) containing 0.05M NaCl, and the solution (toxin A) was filter sterilized and stored at 4° C.

Cell membrane material tested as reagents for binding *C. difficile* toxin A in the present invention were prepared according to the following examples.

EXAMPLE 2

Isolation of Rabbit Erythrocytes

Rabbit blood was obtained from three sources as follows: Heparinized blood was purchased from Pel-Freeze Biological (Rogers, AR). Defibrinated sterile rabbit blood was purchased from Brown Laboratories (Topeka, KA). Fresh rabbit blood (drawn in heparin) was obtained from animals maintained in the inventors' laboratory. Erythrocytes were sedimented from heparinized, defibrinated or fresh whole mammalian blood by centrifugation at 1000 × g for five minutes. The plasma and buffer coat were removed by aspiration. The cells were washed three times in isotonic buffer (10 mM sodium phosphate buffer containing 140 mM NaCl and 3 mM KCl, pH 7.4) at 4° C. prior to use in any toxin A assay.

EXAMPLE 3

Preparation of Hamster Brush Border Membranes

Brush border membranes were isolated from golden Syrian, male hamsters (Engle Laboratory Animals, Inc., Farmersburg, IN) according to the method of Forstner et al, *Biochem.J* 106 381-390 (1968) as follows Hamsters were fasted for 24 hours and sacrificed. The small intestines were excised and rinsed through with ice-cold 0.15M NaCl and cut longitudinally and laid out on a cold glass plate. The mucosa was removed by light scraping using the edge of a glass slide and homogenized in 75 vol. of 5 mM EDTA, pH 7.4 (EDTA-NaOH buffer) for 25 seconds using a powerstat set at 90V and a waring blender. All operations were performed at 4° C. The homogenate was passed through fine nylon to remove large contaminating particles and the filtrate was centrifuged at 400 × g for 10 min. The supernatant was decanted and the cycle of centrifugation and washing was repeated several times in 5 vol. until most of the small size contaminating material was removed as determined by phase contrast microscopy. The washed sediment of crude brush border fraction was suspended in 2 vol. of 90 mM NaCl-0.8 mM EDTA, mixed thoroughly and kept until a well-defined sediment developed. The supernatant and sediment were then poured in succession through a pad of glass wool to remove aggregated particles. After the glass wool pad had been washed with 20 ml of 5 mM EDTA buffer, brush borders in the total washing were sedimented by centrifugation at 450 × x g for 10 min. and washed once with 2.5 vol. of 2.5 mM EDTA buffer. The purified brush border membranes were stored at 4° C. prior to being used in any toxin A assay.

EXAMPLE 4

Preparation of Rabbit Erythrocyte Ghosts

Hemoglobin-free rabbit red blood cell membranes (ghosts) were prepared according to the method of Dodge et al., *Arch.Biochem.Biophys.* 100: 119-130 (1963). The method employs hemolysis of the erythrocytes in hypotonic solution for removal of hemoglobin. Hemolysis was thus performed by pipetting 3 ml aliquots of the washed erythrocyte suspension from Example 2 into 120 ml of cold hypotonic buffer (5 mM sodium phosphate, pH 8.0). The contents were mixed by gentle swirling and allowed to stand at 4° C for 30 min. The hemolyzed cells were then sedimented by centrifugation at 15,000 × g for 30 min. The supernatant was aspirated carefully, and the ghost button was resuspended by swirling while adding back sufficient fresh hypotonic buffer to reconstitute the original volume. The ghosts were washed 3 times subsequent to hemolysis. Sedimented ghosts were creamy white and were finally resuspended in 10 mM sodium phosphate buffered saline (PBS), pH 7.4 and stored at 4° C. prior to use in any toxin A assay.

EXAMPLE 5

Preparation of Rabbit Erythrocyte

Ghosts Minus Peripheral Proteins

Ghosts from rabbit erythrocytes prepared according to Example 4 were stripped of peripheral proteins by the addition of 10 volume of ice-cold 0.1M NaOH as described by Steck and Yu, *J. Supranol. Struc.* 1:220-232 (1973). Integral membrane-bound proteins were sedimented by centrifugation at 20,000 × x g for 30 min and washed 3 times with 10mM PBS, pH 7.4 prior to use.

EXAMPLE 6

Preparation of Inside-Out Vesicles

Inside-out vesicles from rabbit erythrocytes were prepared according to the method of Seymour et al., "Preparation of Inside-Out Vesicles from Red Blood Cells in One Step", pages 219-222 in Ellory et al. (ed.), *Red Cell Membrane-A Methodological Approach*, Academic Press, New York (1982).

Solubilized membrane extracts used as reagents in the present invention were prepared as follows:

EXAMPLE 7

Preparation of Detergent-Solubilized Rabbit Erythrocyte Membrane

Ghosts from rabbit erythrocytes were solubilized 6 hours at 4° C. with 1% (vol/vol) n-octylglucoside (Sigma Chemical Co.) in 20mM sodium phosphate buffer, pH 8.0. The solubilized membranes were centrifuged at 20,000 × g for 30 min. at 4° C. and the supernatant was decanted and stored at 4° C. prior to assay.

EXAMPLES 8-9

Preparation of Total Lipid Membrane Extract

Hamster brush border membranes and rabbit erythrocyte ghosts were extracted for total lipid with chloroform:methanol:$H_2O$ (4:8:3, vol/vol). The lipid extract contained toxin A receptor.

A variety of assay techniques known to those skilled in the art may be used in the method of the present invention for determining binding of toxin A by the various cell membrane materials prepared above. Binding of toxin A by rabbit erythrocyte ghosts and hamster brush border membranes was demonstrated by crossed immunoelectrophoresis ("IEP") according to the procedure of Example 10, infra, and also by rocket IEP and indirect ELISA. Toxin A was specifically removed from *C. difficile* culture filtrate (prepared according to Example 1) by hamster brush border membranes and rabbit erythrocytes as shown by crossed IEP (FIG. 1). None of the other antigens present in the culture filtrate (including toxin B) showed significant reduction in peak height as measured by rocket IEP, whereas toxin A was completely removed. The specific binding of toxin A to hamster brush border membrane types was seen at 4, 22 and 37° C.; however, binding of toxin A to whole rabbit erythrocytes did not occur at 37° C., but only at the lower temperatures.

The specificity of this binding was examined further by incubating toxin A with other membrane preparations. Ghost membranes prepared from rabbit erythrocytes (Example 4) and membranes stripped of peripheral proteins leaving integral proteins intact (Example 5) showed identical binding activity to that of whole erythrocytes (Example 2) and hamster brush border membranes (Example 3). However, inside-out vesicles from rabbit ghosts (Example 6) did not bind significant amounts of toxin A. This suggests that the receptor functions on the external surface of the membrane.

The binding of toxin A to erythrocytes of other species (hamster, human, mouse, rat, sheep, dog,cat,goat, horse, chicken, cow and pig) was also tested. Of the twelve species examined only rabbit erythrocytes bound toxin A as detected by crossed IEP or hemagglutination.

We attempted to elute toxin A bound to rabbit ghost membranes with 10 mM EDTA-lM NaCl, pH 8.0; 50 mM Tris-1M KCl, pH 8.0; 50 mM Tris-lM KSCN, pH 8.0; 50mM Tris-3M KSCN, pH 8.0; and 50 mM Tris-1% Triton X-100 (vol/vol). Of the agents tested, only the Tris-Triton X-100 eluted the toxin (Example 7). At a Triton X-100 concentration of 1% (vol/vol) more than 80% of the binding activity of rabbit ghosts was removed from the insoluble ghost residue as detected by rocket IEP. The loss of binding of toxin A was accomplished by the appearance of toxin-binding material in the supernatant extract. Analysis of the supernatant extract by crossed IEP showed that toxin A, when combined with the supernatant, migrated differently from toxin A, mixed with detergent alone (FIG. 2). These results indicate that the toxin was complexed with an erythrocyte membrane component which is the toxin A receptor.

Binding of toxin A by rabbit erythrocyte ghosts was demonstrated according to Example 10.

EXAMPLE 10

Crossed Immunoelectrophoresis

Binding of toxin A to cells was accomplished by mixing crude *C. difficile* culture filtrate (ca. 2 mg protein/ml) or purified toxin A (0.1–1.0 mg/ml) from Example 1 with hamster brush border membranes or rabbit erythrocyte ghosts in 1.5 ml polypropylene microcentrifuge tubes. Reaction mixtures contained 25 microliters of packed cells, 10 mM PBS, pH 7.4 and toxin in a final volume of 0.1 ml. After incubation for 15 min at room temperature, cells were centrifuged using a Brinkman 5412 Eppendorf centrifuge and the supernatant was assayed for toxin by crossed immunoelectrophoresis on 5 ×5 cm glass slide as described by Lyerly et al., *A.J.Clin. Microbiol.* 17:72-78 (1983). Briefly, wells (1 mm in diameter) are cut in gels composed of 1.2% (wt/vol) low electroendosmotic agarose (Sigma Chemical Co.) in 0.025M Tris-Tricine buffer (pH 8.6). For the first dimension, samples (4 microliters) are placed in the wells and subjected to electrophoresis at 9 to 10V/cm for 45 minutes at 10° C. In the second dimension, the upper part of each gel (11.6 $^{2}$) is composed of a 1.2% agarose gel (3.4 ml) containing 50 microliters of antiserum or toxin A antibody preparation. Electrophoresis is performed at 2 V/cm for. 18 h at 4° C. Gels are pressed, washed, stained and destained.

The biochemical assays described in the following Examples 11 through 16 may be used in the method of the present invention to detect the presence of toxin A.

EXAMPLE 11

Receptor-ELISA

The wells of a polystyrene microtiter plate (Immulon type 2; Dynatech Industrie, Alexandria, VA) were coated overnight at 37° C. with 0.3 ml of membrane-extracted receptor (Example 8) in PBS, pH 7.4. Control wells were incubated with PBS and served as background controls for nonspecific binding of all subsequent reagents. The plates were washed once with 0.3 ml of PBS-0.5% (vol/vol) Tween 20 (PBS-T). The remaining unbound reaction sites were blocked by the addition of 0.3 ml of 1% bovine serum albumin (BSA) to all wells for 1h at 37° C. The wells were emptied and washed as above after which a fecal sample obtained from a patient with diarrhea under antibiotic therapy at Mayo Clinic was added and incubated for 1 h at 4° C. or room temperature (20° C). After incubation the wells are washed 4 times with PBS-T, and 0.2 ml of a 1/500 dilution (in PBS-T containing 0.1% vol/vol neutral rabbit serum) of toxin A antibody was added to each well. After incubation for 1h at 4° C., or room temperature, the wells were washed as described above, and 0.2 ml of a 1/500 dilution (in PBS-T containing 0.1% neutral rabbit serum) of rabbit anti-goat IgG-alkaline phosphatase conjugate (Sigma Chemical Co.) was added. The plates were incubated for 1h at 4° C. or room temperature and washed as described above, and 0.2 ml of a 1 mg/ml (in diethanolamine buffer, pH 9.8) of p-nitrophenyl phosphate (Sigma Phosphatase 104 substrate) was added to each well. The plates were incubated for 30 min. at room temperature, and the reaction was terminated by addition of 5N NaOH to each well. The optical density (OD) was measured with a spectrophotometer at a wavelength at 405 nm. Plates were also read visually for yellow color, and a positive or negative result was recorded.

EXAMPLE 12a

Hemagglutination Assay

Erythrocytes are washed 4 times in 10 volumes of TBS, pH 7.2, and diluted to a 2.5% suspension. Two-fold serial dilutions of toxin A (50 microliters) were performed with Tris-buffered saline ("TBS") in V-bottom microtiter plates (Cooke Laboratories, Alexandria, VA) and 50 microliters of fresh washed erythrocytes are added to each well. The plates are gently tapped and the red blood cells are allowed to settle at either 4, 22, or 37C. Titers are expressed as the reciprocal of the highest dilution of toxin A in which hemagglutination is visible macroscopically When *C. difficile* antiserum is used, the above hemagglutination assay is performed in slightly modified form as follows.

EXAMPLE 12b

Hemagglutination Assay

Toxin A is diluted in TBS (in two-fold series) in small 12 ×75 mm glass test tubes and each tube is mixed with an equal volume of a 5% freshly washed rabbit erythrocyte suspension. After 5 min. at room temperature or 4° C., 50 microliter aliquots of erythrocyte suspension are added to V-bottom mircotiter plates which contain either TBS of C. difficile 10463 antitoxin (1:2000 dilution for room temperature or 1:500 dilution for 4° C. in TBS). The suspensions are mixed by tapping the plates and the erythrocytes are allowed to settle.

EXAMPLE 13

Slide Agglutination

Washed rabbit erythrocytes or erythrocyte ghosts may be used in this assay. Cells (0.05 ml) are mixed with 1 ml of test antigen (culture filtrate or fecal sample) in 1.5 ml polypropylene Eppendorf centrifuge tubes. After incubation at 4° C. for 35 min., the cells are sedimented by centrifugation (Brinkman 5412 Eppendorf centrifuge), the supernatant decanted, and the cell pellet resuspended in 0.05 ml of a 1/500 dilution of goat antiserum against crude *C. difficile* toxin. The cell suspension is then placed on a slide and rotated for 5 min. Visible or microscopic clumping of the cells is taken as positive for the presence of toxin A in the test antigen solution Absence of clumping is graded as negative for the presence of toxin A. Dyes may be added to the slide to enhance the visibility of agglutination. For example, one drop of 1/100 dilution of crystal violet may be mixed with the suspension. The appearance of violet clumps is indicative of a positive test for the presence of toxin A in the test specimen.

EXAMPLE 14

Slide Coagglutination

Washed rabbit erythrocytes or erythrocyte ghosts are treated exactly as in Example 11 with the test antigen; however, after centrifugation, the cell pellet is resuspended in PBS instead of goat antiserum. The cell suspension (0.50 ml) is placed on a slide to which 0.05 ml of a 4% latex bead suspension is added, the latex beads having been coated with goat antiserum against crude *C. difficile* toxin. The slide is rotated for 5 min. and visible or microscopic clumping or rabbit cells with latex beads (coagglutination) is regarded as positive for the presence of toxin A in the test specimen.

A variation of the coaggultination assay of Example 14 employs membrane-bound toxin A receptor, membrane-extracted toxin A receptor, or purified toxin A receptor which has been immobilized or entrapped on a particulate surface. Such particles include magnetic beads, gelatin particles, liposomes, latex beads, bacterial cells, or other erythrocytes or mammalian cells. A specimen is allowed to incubate with the particle-bound receptor and then tested on a slide with goat antiserum containing toxin A antibody. Visible or microscopic clumping, or the presence of a colored product, is regarded as positive for the presence of toxin A in the specimen. Example 15 illustrates one such method using rabbit erythrocytecontaining liposomes.

EXAMPLE 15

Slide Coaggulation With Rabbit Erythrocyte Receptor-Containing Liposomes

Solubilized rabbit erythrocyte membranes prepared according to Example 5 are dialyzed against distilled water at room temperature until a white precipitate forms. The receptor-containing precipitate is introduced into liposomes prepared by the method described by Poste et all, "Lipid Vesicles As Carriers For Introducing Biologically Active Materials Into Cells" , in Prescott (ed.), *Methods In Cell Biology*, Vol. XIV (1976). In brief, multilamellar liposomes composed of DL-alpha-phosphatidylcholine, stearylamine, cholesterol (63:18:19). (Sigma Chemical Co.) are made by dissolving 10 micromoles of the lipid in 1 ml of HPLC-grade chloroform (preserved with 1% ethanol) with the white precipitate in a roundbottom flask. After evaporation under vacuum, the dried lipid is dispersed in 10 mM PBS, pH 7.4, using a vortex mixer. The multilamellar liposome suspension containing the rabbit erythrocyte receptor gives a milky appearance which is free of particulate matter. The liposomes are mixed with toxin A on a glass slide at 4° C. After mixing, antisera containing toxin A antibody is added to the slide and agglutination occurs.

Unilamellar liposomes containing the receptor may be most advantageously prepared using any of the presently-available devices for manufacturing such bodies One such device suitable for this purpose is the "Lipoprep GD-1" from Dianorm Scientific Instruments, Munich, W. Germany. Any toxin A receptor material can be advantageously mixed with lipid and made into liposome suspensions containing the receptor. The thus-immobilized receptor material may be used as a reagent to detect, isolate or purify *C. difficile* toxin A according to the present invention Conversely, toxin A-liposomes may be prepared by the same method and used to detect, isolate or purify materials containing the receptor structure.

EXAMPLE 16

Indirect Immunofluorescence

Washed rabbit erythrocytes or erythrocyte ghosts may be used for this assay. Cells (0.50 ml) are mixed with 1 ml of the specimen solution in Eppendorf centrifuge tubes. After incubation at room temperature for 30 min., the cells are sedimented by centrifugation, the supernatant is decanted, and the cell pellet is resuspended in 0.50 ml of a 1/500 dilution of goat antiserum against crude *C. difficile* toxin A. After incubation for 35 min. at 4° C., the cells are washed in PBS, pH 7.4, and 0.02 ml of cell suspension is spread on a microscope slide and heat fixed by passing the slide over the flame of a Bunsen burner. To the slide, 0.05 ml of a 1/50 dilution (in PBS pH 7.4) of rabbit anti-goat IgG fluroescein isothiocyanate conjugate (FITC) is added and the slide is incubated in a moist chamber for 30 min. at 4° C. After incubation, the slide is washed twice with PBS and mounted on a fluorescent microscope for observation. Fluorescent cells are indicative for the presence of toxin A in the test specimen.

The binding of toxin A to hamster brush border membranes and to rabbit erythrocyte membranes is specific, because only toxin A is removed from *C. difficile* culture filtrate and adsorbed to these cell types. Rabbit erythrocytes appear to be unique because erythrocytes from 12 other species did not bind toxin A.

The present invention provides a simple and rapid method for large-scale purification of *C. difficile* toxin A, or conversely, for purification containing the Gal-alpha-1-3Gal structure.

Typically, the receptor-containing reagents are found in biological materials such as membranes, organs, cells or the like which are extracted by suitable detergents, solvent or buffers to soluabalize the fractions which include reagents containing the Gal-alpha-1-3Gal structure Such preliminary extrusion and crude purification procedures are known to those skilled in the art. The crude extract is solubilized or suspended in a suitable liquid and contacted with immobilized *C. difficile* toxin A at a temperature favoring reversible binding to the immobilized toxin A. Toxin A is preferably immobilized on a suitable substrate disposed in the form of an affinity column. The Gal-alpha-1-3-Gal structure binds to the column while other components of the extract are permitted to pass through the column. The temperature is then increased to release the bound reagent, which is eluted in substantially pure form.

Examples 17 and 18 illustrate the purification of thyroglobulin from calf thyroid glands and laminin from mouse EHS tumors using a toxin A affinity column.

EXAMPLE 17

Purification of Calf Thyroglobulin

A toxin A affinity column is prepared as follows. Affi-gel 15 activated affinity support (Bio-Rad Laboratories) is added to purified toxin A (2–3 mg toxin/ml gel) in 0.1M 3-[N-morpholino]propane sulfonic acid ("MOPS") at 4° C. The gel is agitated gently on a rocker for four hours at 4° C. Blocking is accomplished by adding 0.1 ml of 1M ethanolamine, pH 8, per ml of gel. After one hour, the gel is transferred to a column and washed with Tris-buffered saline (0.1 M Tris and 0.05M NaCl, pH 7). Thyroid glands surgically removed from calves are frozen and thinly sliced in the frozen state. The slices are extracted with 0.9% NaCl overnight, with stirring at 4° C. After centrifugation of the mixture at 78,000 × g for 1 hour, the supernatant fluid is carefully loaded on the the *Clostridium difficile* toxin A affinity column at 4° C. The supernatant is allowed to pass through the column. The column is then thoroughly washed with Tris-buffered saline and the effluent is monitored at 280 nm. Washing is repeated as necessary until the effluent is free of protein. The column is then brought to 37° C. and substantially pure thyroglobulin is eluted off.

EXAMPLE 18

Purification of Laminin From Mouse EHS Tumors

Mouse EHS tumors (ATCC, Bethesda, MD) are homogenized in 3.4M NaCl, 0.01 M phosphate buffer, pH 7.4, with 50 micrograms/ml phenylmethylsulfonyl fluoride ("PMSF", Sigma Chemical, St. Louis, Mo.) and 50 micrograms per ml of p-hydroxymercuribenzoate (Sigma). The tumors are washed once with the same buffer, and then extracted overnight with 0.5M NaCl, 0.01 M phosphate pH 7.4 and 50 micrograms ml each of PMSF and phydroxymercuribenzoate. Type IV collagen is removed from the extract by raising the salt concentration to 1.7 M, followed by stirring for one hour at 4° C. and centrifugation (10,000 rpm, 30 min.). Laminin is precipitated from the extract with 30% saturated ammonium sulfate. The precipitate is resuspended in 0.5M NaCl, 0.01M phosphate pH 7.4, and dialyzed against the same buffer. The dialyzied extract is then applied to a toxin A affinity column prepared in accordance with the procedure of Example 17. Substantially pure laminin is then obtained from the column in the same manner that thyroglobulin was obtained in Example 17.

*C. difficile* toxin A is conveniently purified according to the present invention by contacting an immobilized reagent containing an available non-reducing Gal-alpha-13Gal structure with a source of soluble toxin A, e.g., cell culture filtrate, at a temperature favoring reversible binding. The reagent is preferably immobilized on a suitable substrate disposed in the form of an affinity column. Toxin A binds to the column as the filtrate passes through. The temperature is then increased to release the bound toxin, which is eluted in substantially pure form.

Rabbit erythrocyte ghosts may be used to purify toxin A according to Example 19.

EXAMPLE 19

Purification of Toxin A From Culture Filtrate By Rabbit Erythrocyte Ghosts

Rabbit erythrocyte ghosts from Example 4 are mixed with crude toxin A culture filtrate at 4° C. and centrifuged at 15,000 rpm/minute for 10 minutes. The supernatant fluid is decanted from the ghost pellet, and the latter is washed in excess TBS (pH 7). The supernatant fluid is decanted. The ghosts are resuspended in a small volume of PBS, warmed to 37° C. and centrifuged as before. The resulting supernatant is substantially pure toxin A.

Toxin A is most advantageously isolated and purified in substantially pure form by affinity chromatography using immobilized Gal-alpha-1-3Gal structure-containing reagents. The following example illustrates this principle using a thyroglobulin affinity column:

EXAMPLE 20

Purification of Toxin A From Culture Filtrate By Thyroglobulin Affinity Chromatography A thyroglobulin affinity column is prepared as follows. Affi-gel 15-activated affinity support (Bio-Rad Laboratories) is added to purified thyroglobulin (25 mg thyroglobulin/ml gel) in 0.1 M 3-[N-morpholino]propane sulfonic acid ("MOPS") at 4° C. The gel is agitated gently on a rocker for four hours at 4° C. Blocking is accomplished by adding 0.1 ml of 1M ethanolamine, pH 8, per ml of gel. After one hour, the gel is transferred to a column and washed with Trisbuffered saline (0.1M Tris and 0.05 M NaCl, pH 7). The crude filtrate from *C. difficile* VPI strain 10463 (see Example 1) is carefully loaded on the thyroglobulin affinity column at 4° C. and allowed to pass through the column. The column is then thoroughly washed with Tris-buffered saline and the effluent is monitored at 280 nm. Washing is repeated as necessary until the effluent is free of protein. The column is then brought to 37° C. and substantially pure *C. difficile* is eluted off.

All references herein cited with respect to synthetic or analytical procedures are incorporated herein by reference.

The present invention may be embodied in other specific forms without departing from the spirit or essential attributes thereof, and, accordingly, reference should be made to the appended claims, rather than to the foregoing specification, as indicating the scope of the invention.

We claim:

1. A method of detecting *Clostridium difficile* toxin A, which method does not detect toxin B, comprising:
   (a) contacting a specimen with a reagent containing an available non-reducing galactose-alpha-1-3-galactose-beta-1-4-Nacetyl glucosamine structure;
   (b) assaying for binding of *C. difficile* toxin A to the reagent.

2. A method according to claim 1 wherein the reagent is selected from the group consisting of erythrocytes, erythrocyte ghosts, brush border membranes, thyroglobulin, laminin and collagen.

3. A method according to claim 2 wherein the erythrocytes and erythrocyte ghosts are rabbit erythrocytes and erythrocyte ghosts.

4. A method according to claim 2 wherein the brush border membrane is a hamster brush border membrane.

5. A method according to claim 1 wherein the reagent comprises purified *C. difficile* toxin A receptor.

6. A method according to claim 1 wherein the assaying means of step (b) is selected from the group consisting of enzyme-linked immunosorbent assay, hemagglutination, slide agglutination, slide coagglutination, indirect immunofluorescence, latex agglutination, and liposome agglutination.

7. A method according to claim 2, wherein the reagent is selected from the group consisting of erythrocytes and erythrocyte ghosts and step (b) comprises adding antisera containing toxin A antibody from another species, whereby agglutination of said erythrocyte or erythrocyte ghosts indicates the presence of toxin A in the specimen.

8. A method according to claim 1 wherein contact in step (a) is below about 20° C.

9. A method according to claim 8 wherein contact is between about 0° C. and 15° C.

10. A method according to claim 1 wherein the sample is feces.

11. A method for detecting *C. difficile* toxin A, which method does not detect toxin B, comprising:
   (a) contacting a specimen with a material selected from the group consisting of rabbit erythrocytes, rabbit erythrocyte ghosts, and brush border membranes; and
   (b) assaying for binding of *C. difficile* toxin A.

12. A method according to claim 11 wherein the reagent is rabbit erythrocyte or rabbit erythrocyte ghosts.

13. A method according to claim 11 wherein the reagent is rabbit is a erthrocyte or rabbit erythrocyte ghosts.

14. A method for isolating or purifying a reagent containing an available non-reducing galactose-alpha-1-3-galactose-beta-1-4-N-acetyl glucosamine structure comprising:
   (a) contacting materials which may contain the reagent with immobilized *C. difficile* toxin A at a temperature favoring reversible binding of the reagent to the toxin A;
   (b) increasing the temperature to release the reagent from the immobilized toxin A;
   (c) eluting the reagent.

15. A method according to claim 14 wherein the temperature in step (a) is below about 20° C.

16. A method according to claim 15 wherein the temperature in step (a) is 0–15° C.

17. A method according to claim 16 wherein the temperature is increased in step (b) to above about 30° C.

18. A method according to claim 17 wherein the temperature in step (b) is increased to between about 30° C. and about 37° C.

19. A method according to claim 14 wherein the toxin A is immobilized on a substrate to form an affinity chromatography column.

20. A method for isolating or purifying *C. difficile* toxin A comprising:

(a) contacting a source of toxin A with immobilized reagent containing an available non-reducing galactose-alpha-1-3-galactose-beta-1-4-N-acetyl glucosamine structure at a temperature favoring reversible binding of toxin A to the immobilized reagent;

(b) increasing the temperature to release toxin A bound to the immobilized reagent;

(c) eluting toxin A

21. A method according to claim 20 wherein the temperature in step (a) is below about 20° C.

22. A method according to claim 21 wherein the temperature in step (a) is 0° C.–15° C.

23. A method according to claim 22 wherein the temperature is increased in step (b) to above about 30° C.

24. A method according to claim 23 wherein the temperature is increased in step (b) to between about 30° C. and about 37° C.

25. A method according to claim 20 wherein the immobilized reagent is disposed in the form of an affinity column.

26. A method according to claim 25 wherein the reagent is thryroglobulin.

27. A method according to claim 21 wherein the reagent is immobilized on a substrate to form an affinity chromatography column.

28. A method according to claim 27 wherein the reagent is thyroglobulin.

29. A method according to claim 27 wherein the reagent is laminin.

* * * * *

UNITED STATES PATENT AND TRADEMARK OFFICE
CERTIFICATE OF CORRECTION

PATENT NO. : 4,863,852

DATED : September 5, 1989

INVENTOR(S) : Tracy D. Wilkins et al.

It is certified that error appears in the above-identified patent and that said Letters Patent is hereby corrected as shown below:

Column 1, line 29, change "etilology" to --etiology--; line 39, insert --.-- after "tract"; line 59 change "diahhrea" to --diarrhoea--. Column 2, line 12, insert --recent-- after "more"; line 18, insert --.-- after sample. Column 4, line 18, change "quantitativly" to --quantitatively--; line 68, change "solubolization" to --solubilization--. Column 5, line 54, change "fluoroescein" to --fluorescein--. Column 6, line 46, change "ph" to --pH--; line 56, change "Thryoglobulin" to --Thyroglobulin--; line 61, change "substantial" to --substantially--. Column 7, line 22, change "inoculumn" to --inocculumn--; line 33, change "40°" to --4°--; line 42, change "Afer" to --After--. Column 8, line 14, change "buffer" to --buffy--. Column 9, line 19, delete "x" before "g". Column 11, line 22, change "are" to --were--; lines 52-53, change "4, 22, or 37C" to --4°C, 22°C, or 37°C--. Column 12, line 31, change "11" to --13--; line 34, change "0.50" to --0.05--; line 41, change "coaggultination" to --coagglutination--; line 61, change "5" to --7--. Column 13, lines 43-44, change "fluroescein" to --fluorescein--; line 63, change "soluabalize" to --solubilize--. Column 14, line 49, change "micrograms ml" to --micrograms/ml--; line 50, change "phydroxymercuribenzoate" to --p-(hydroxymercuri)benzoate; line 57, change "dialyzied" to --dialyzed--. Column 15, line 40, change "Trisbuffered" to --Tris-buffered--.

UNITED STATES PATENT AND TRADEMARK OFFICE
CERTIFICATE OF CORRECTION

PATENT NO. : 4,863,852

DATED : September 5, 1989

INVENTOR(S) : Tracy D. Wilkins et al.

It is certified that error appears in the above-identified patent and that said Letters Patent is hereby corrected as shown below:

Column 15, line 64, claim 1, change "1-4-Nacetyl" to --1-4-N-acetyl--.
Column 16, lines 41-42, claim 13, change "rabbit is a erthrocyte or rabbit erythrocyte ghosts" to --a brush border membrane--. Column 18, line 8, claim 26, line 2, change "thryroglobulin" to --thyroglobulin--.

Signed and Sealed this

Sixteenth Day of April, 1991

Attest:

HARRY F. MANBECK, JR.

Attesting Officer

Commissioner of Patents and Trademarks